(12) United States Patent
Fuerst

(10) Patent No.: US 10,431,340 B2
(45) Date of Patent: Oct. 1, 2019

(54) SYSTEMS FOR PREDICTING HYPOGLYCEMIA AND METHODS OF USE THEREOF

(71) Applicant: Eco-Fusion, Ramat Gan (IL)

(72) Inventor: Oren Fuerst, Ramat Hasharon (IL)

(73) Assignee: Eco-Fusion, Ramat Gan (IL)

( * ) Notice: Subject to any disclaimer, the term of this patent is extended or adjusted under 35 U.S.C. 154(b) by 340 days.

(21) Appl. No.: 15/121,225

(22) PCT Filed: Feb. 27, 2015

(86) PCT No.: PCT/IB2015/000932
§ 371 (c)(1),
(2) Date: Aug. 24, 2016

(87) PCT Pub. No.: WO2015/128740
PCT Pub. Date: Sep. 3, 2015

(65) Prior Publication Data
US 2017/0068790 A1  Mar. 9, 2017

Related U.S. Application Data

(60) Provisional application No. 61/946,565, filed on Feb. 28, 2014.

(51) Int. Cl.
| | |
|---|---|
| *G01N 33/48* | (2006.01) |
| *G16H 50/20* | (2018.01) |
| *G16H 50/30* | (2018.01) |
| *G06F 19/00* | (2018.01) |
| *G16H 10/60* | (2018.01) |

(52) U.S. Cl.
CPC ......... *G16H 50/20* (2018.01); *G06F 19/3418* (2013.01); *G16H 50/30* (2018.01); *G06F 19/3456* (2013.01); *G16H 10/60* (2018.01)

(58) Field of Classification Search
None
See application file for complete search history.

(56) References Cited

U.S. PATENT DOCUMENTS

| | | |
|---|---|---|
| 2013/0018668 A1 | 1/2013 | Goldberg et al. |
| 2013/0231947 A1 | 9/2013 | Shusterman |

OTHER PUBLICATIONS

International Search Report and Written Opinion from International Application No. PCT/IB2015/000932 dated Nov. 6, 2015.

*Primary Examiner* — Larry D Riggs, II
(74) *Attorney, Agent, or Firm* — Greenberg Traurig, LLP

(57) ABSTRACT

The present invention provides for a computer system that includes at least one server having software stored on a non-transient computer readable medium; where, upon execution of the software, the at least one server is at least configured to: i) receiving, in real-time, an input from a user; ii) receiving, in real-time, physiological data representative of a physiological measurement of physiological characteristic of the user; iii) comparing, in real-time, the physiological measurement of the user to a pre-determined physiological value associated with the physiological characteristic retrieved from a database; iv) based on the comparing, determining, in real-time, that a difference between the physiological measurement of the user and the pre-determined physiological value is higher or smaller than the predetermined threshold value, and then: v) generating, in real-time, at least one alert; vi) transmitting, in real-time, the at least one alert.

6 Claims, 7 Drawing Sheets

SYSTEMS FOR PREDICTING HYPOGLYCEMIA AND METHODS OF USE THEREOF

RELATED APPLICATIONS

This application claims the priority of U.S. provisional application U.S. Patent Appln. No. 61/946,565; filed Feb. 28, 2014; entitled "SYSTEM AND METHOD OF PREDICTING HYPOGLYCEMIA," which is incorporated herein by reference in its entirety for all purposes.

TECHNICAL FIELD

In some embodiments, the instant invention is related to computer methods/systems to predict hypoglycemia.

BACKGROUND

Individuals with type 1 diabetes adhering to strict glycemic control are prone to suffer severe hypoglycemia. Other well-established risk factors for hypoglycemia include a history of severe hypoglycemia and impaired awareness of hypoglycemia. The role of hypoglycemia may be a factor predisposing young adults to sudden arrhythmic death.

SUMMARY OF INVENTION

In some embodiments, the instant invention provides for a computer system, including: a) at least one server having software stored on a non-transient computer readable medium; where, upon execution of the software, the at least one server is at least configured to: i) receiving, an input from a user, where the input includes user data consisting of: food intake of the user, glucose readings of the user, medication intake by the user, stress related events in the preceding day, insulin dose taken by the user, or any combination thereof; ii) receiving, in real-time, physiological data representative of at least one physiological measurement of at least one physiological characteristic of the user, where the at least one physiological characteristic is selected from the group consisting of: heart rate, heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a computer method, including: i) receiving, an input from a user or from his medical record, where the input includes user data consisting of: food intake of the user, stress related events in the preceding day, glucose readings of the user, medication intake by the user, insulin dose taken by the user, or any combination thereof; ii) receiving, in real-time, physiological data representative of at least one physiological measurement of at least one physiological characteristic of the user, where the at least one physiological characteristic is selected from the group consisting of: heart rate, heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a computer system, including: a) at least one server having software stored on a non-transient computer readable medium; where, upon execution of the software, the at least one server is at least configured to: i) receiving, in real-time, an input from a user, where the input includes user data consisting of: food intake of the user, glucose readings of the user, medication intake by the user, insulin dose taken by the user, or any combination thereof; ii) receiving, in real-time, physiological data representative of at least one physiological measurement of at least one physiological characteristic of the user, where the at least one physiological characteristic is selected from the group consisting of: heart rate, heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a computer method, including: i) receiving, in real-time, an input from a user, where the input includes user data consisting of: food intake of the user, glucose readings of the user, medication intake by the user, insulin dose taken by the user, or any combination thereof; ii) receiving, in real-time, physiological data representative of at least one physiological measurement of at least one physiological characteristic of the user, where the at least one physiological characteristic is selected from the group consisting of: heart rate, heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DESCRIPTION OF EXEMPLARY EMBODIMENTS

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

In some embodiments, the present invention is an alert mechanism for hypoglycemia. In some embodiments, the present invention is a non-invasive alert system for hypoglycemia. In some embodiments, the present invention is an alarm system. In some embodiments, the present invention is configured to save the lives of diabetics.

In some embodiments, the present invention is an alert mechanism for nocturnal hypoglycemia. In some embodiments, the alert mechanism is based on a deviation from the calculated expected value of at least one of the following: heart beat, heart beat variability, low frequency heart beat, high frequency heart beat variability, and blood saturation level. In some embodiments, the present invention is based on at least one of the following input parameters: last measurement of the glucose level, food eaten prior to going to sleep, physical activity during the preceding day, and stress level prior to going to sleep.

Figure 1:
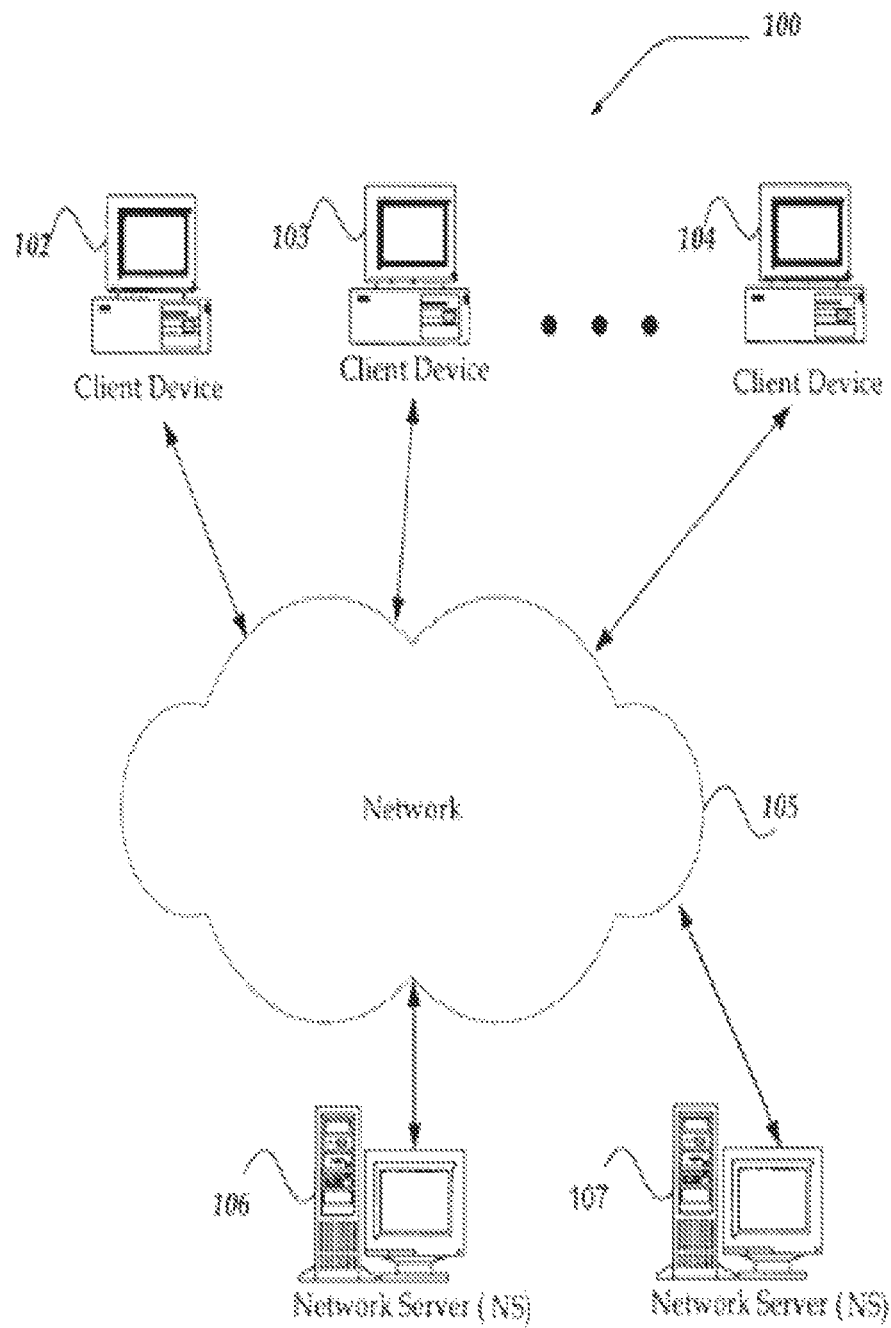
FIGS. 1 and 2 illustrates some embodiments of the inventive system of the present invention, showing users with type 1 diabetes connecting over network servers in accordance with the invention.

FIG. 1 illustrates an embodiment of the present invention.

Figure 2:
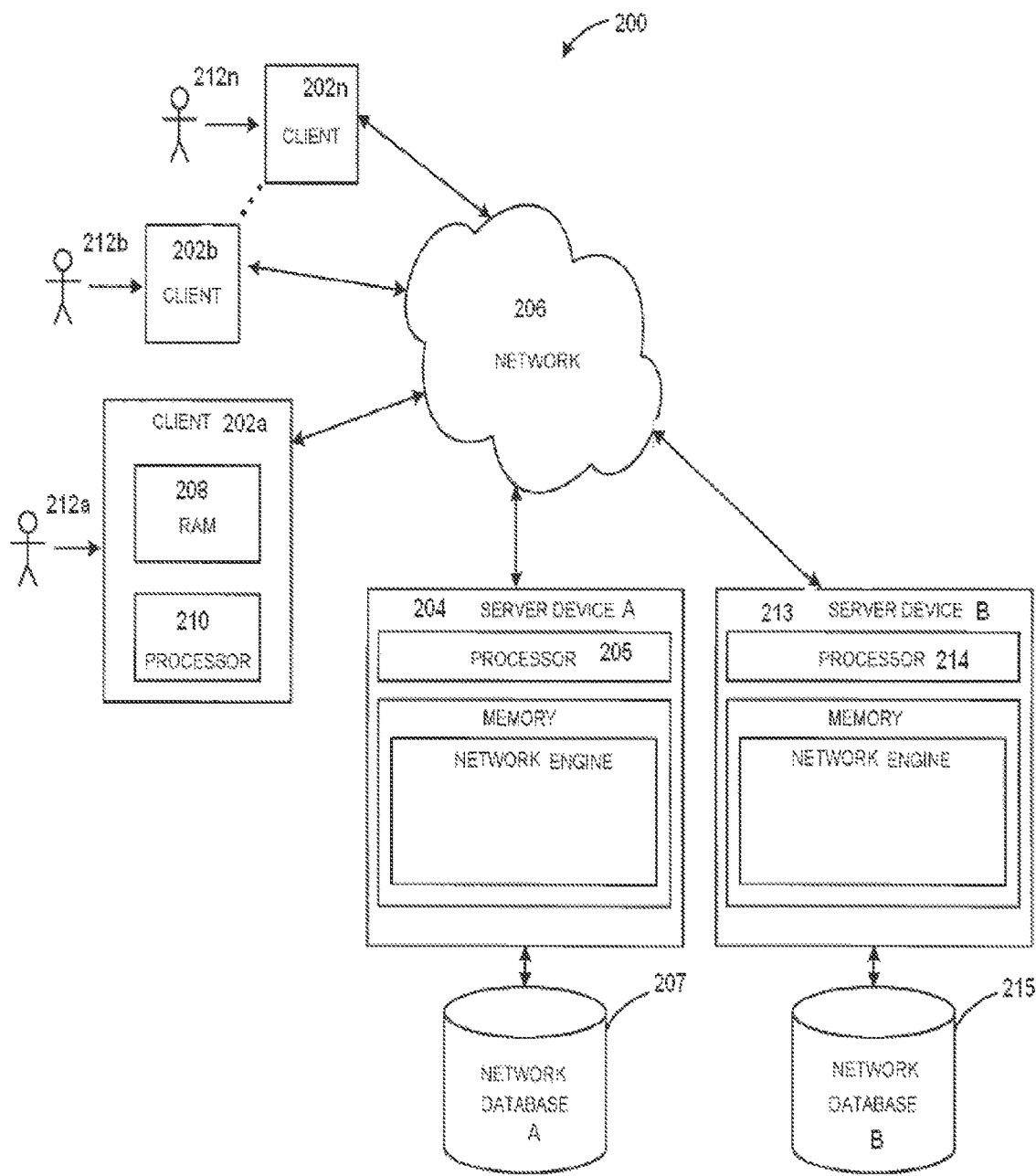

FIG. 2 illustrates an embodiment of the network architecture of the present invention.

Figure 3:
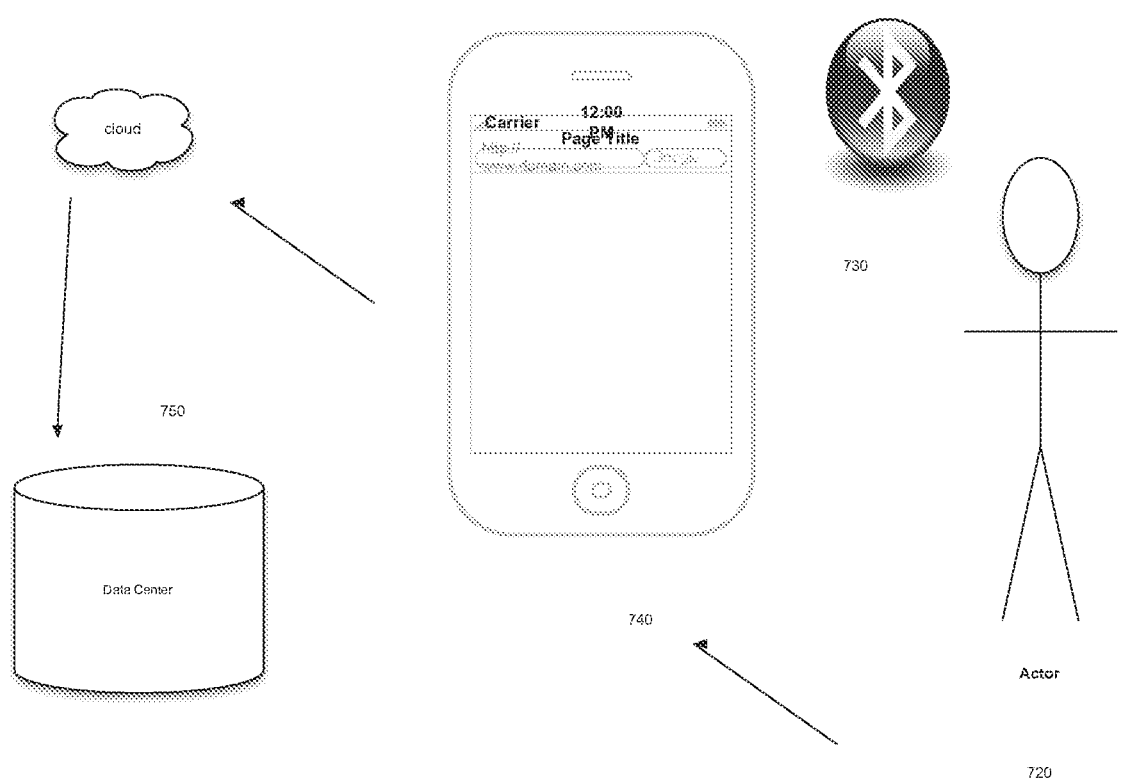
FIG. 3 illustrates some embodiments of the inventive system of the present invention, showing a system receiving inputs provided by a user diagnosed with type 1 diabetes.

FIG. 3 illustrates an embodiment of the system of the present invention.

Figure 4:
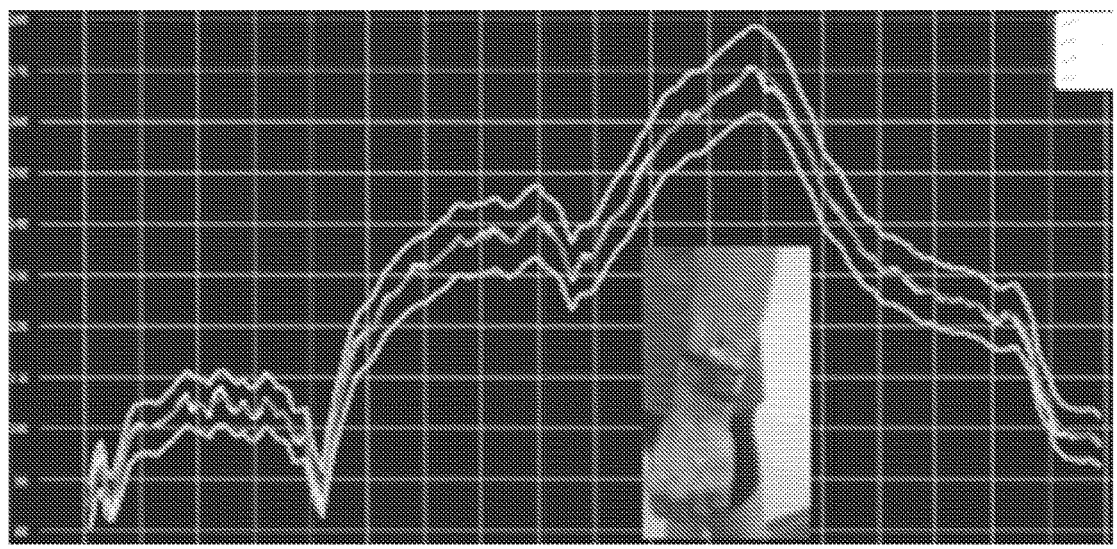
FIG. 4 illustrates some embodiments of the inventive system of the present invention, showing a wristband configured to include the system of the present invention.

FIG. 4 is an embodiment of a hand with the wristband.

Figure 5:
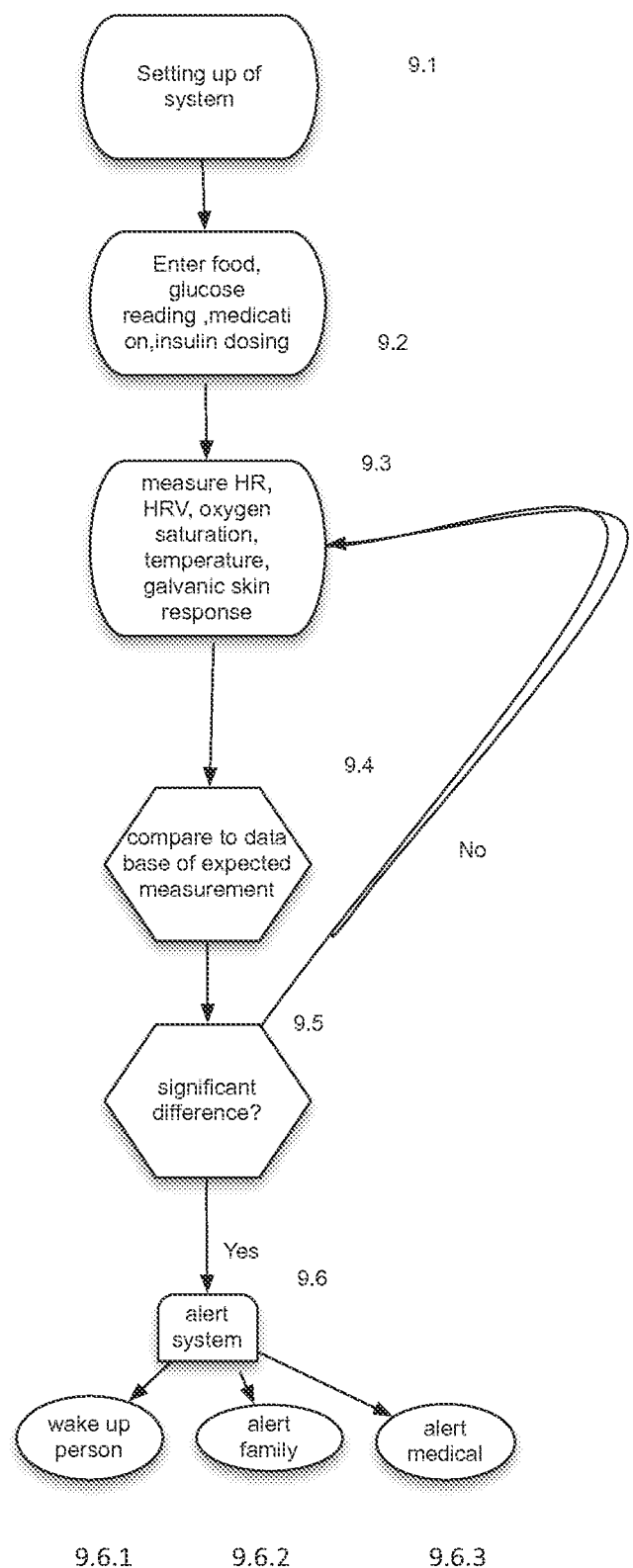
FIG. 5 illustrates a flow diagram of an embodiment of the inventive system of the present invention.

FIG. 5 is a block flow diagram of the process of the present invention.

Figure 6:
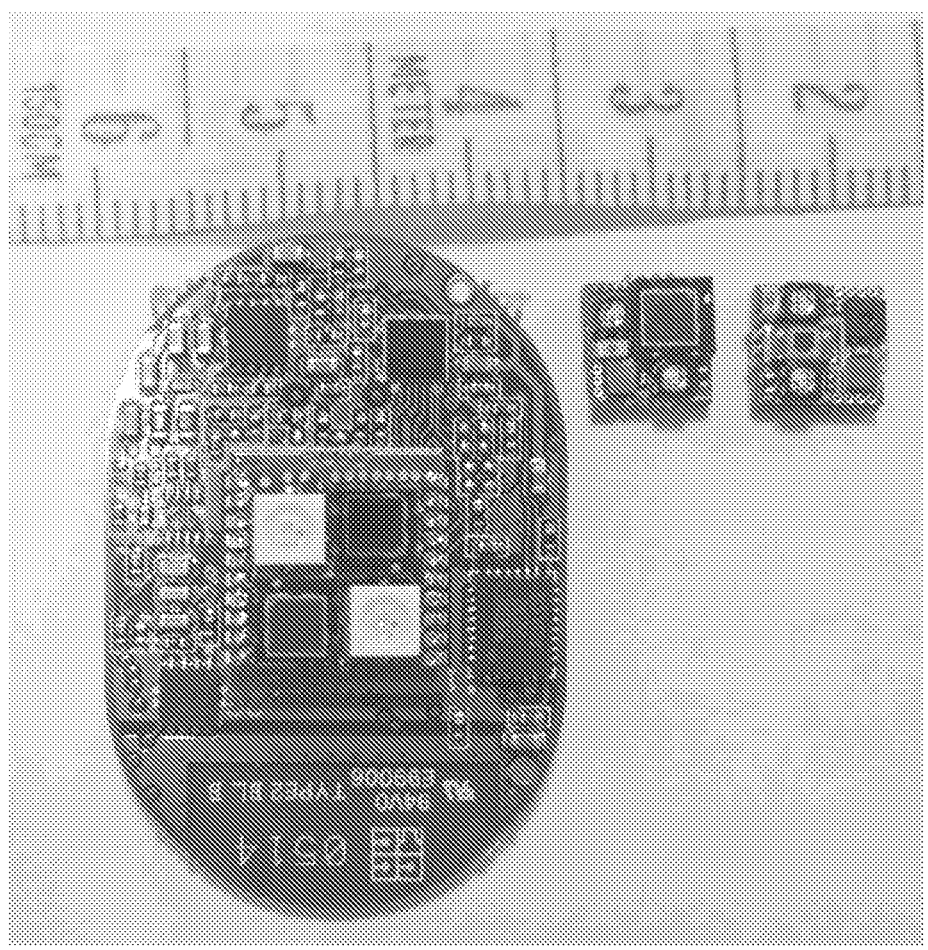
FIG. 6 illustrates an embodiment of the inventive system of the present invention, showing sensors for use in connection with the system.

FIG. 6 is an embodiment of a view of a sample of typical PPG (Photoplethysmography) sensors with Motion immunity using a 3d Accelerometer sensor. In some embodiments, the sensor can be used as a sensor to detect Heart Rate Variability (HRV). In some embodiments, additional sensors can be added to include other parameters, such as blood oxygen.

Figure 7:
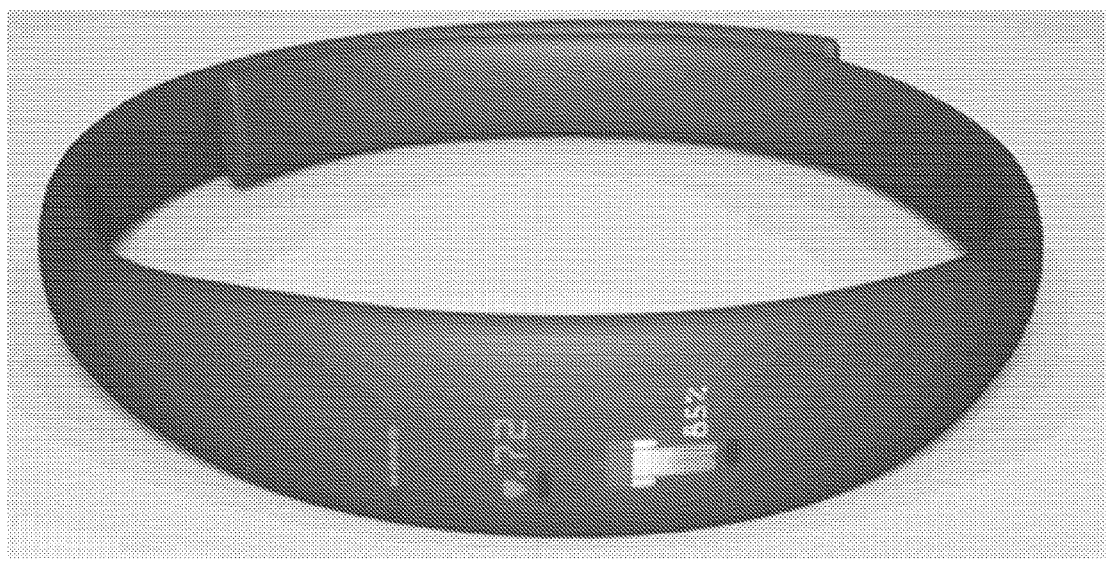
FIG. 7 illustrates an embodiment of a watch configured to use the inventive system.

FIG. 7 illustrates an embodiment of a wrist-band of the present invention.

Hypoglycemia

Individuals with type 1 diabetes adhering to strict glycemic control are prone to suffer from severe hypoglycemia. Other typical risk factors for hypoglycemia include a history of severe hypoglycemia and impaired awareness of hypoglycemia. Despite advanced technology and new insulin analogs, the fear of hypoglycemia is still a problem which complicates the management of diabetes. Without being bound by theory, the role of hypoglycemia may be a factor predisposing young adults to sudden arrhythmic death.

People diagnosed with type 1 diabetes require daily insulin injections to manage their condition. The short-term complication of administering insulin injections is hypoglycemia (i.e., low blood glucose levels). Undetected and/or untreated hypoglycemia can lead to seizures, comas, and hospitalization. People with type 1 diabetes typically have between a 14% to 50% chance of experiencing hypoglycemia at night, and only a few of events are identified. At night, people with type-1 diabetes are at increased risk of undetected hypoglycemia as they are asleep and their autonomic responses are reduced. Between 2% and 4% of people with type-1 diabetes die due to hypoglycemia. According to recent reports, as many as 6% to 10% of deaths in individuals with type-1 diabetes result from hypoglycemia. Thus, hypoglycemia is one of the most dangerous, costly, and difficult diabetes complications to manage.

In some embodiments, the inventive system of the present invention allows for the monitoring of symptoms of hypoglycemia, which may be idiosyncratic/unique/personalized to a person, but people generally learn to recognize his/her unique symptoms. In some embodiments, symptoms of hypoglycemia are neurogenic (autonomic) symptoms which, for example, may include, but are not limited to, palpitations, tremor, hunger, and sweating. In some embodiments, neuroglycopenic symptoms typically include behavioral changes, difficulty thinking, confusion, or any combination thereof. In some embodiments, neuroglycopenic manifestations can include seizure, coma, and even death. In some embodiments, hypoglycemia (in people diagnosed with type 1 diabetes) is the result of the interplay of relative or absolute insulin excess and included physiological defenses against falling plasma glucose concentrations. In some embodiments, a typically used concentration to define the lower limit of normal glucose is 70 mg/dl (3.9 mmol/l), though in someone with diabetes, hypoglycemic symptoms can occur at higher glucose levels, or may fail to occur at lower. In some embodiments, concentration to define the lower limit of normal glucose can be in the range of 80 mg/dl to 120 mg/dl (4.4 mmol/l to 6.7 mmol/l). In some embodiments, a lower limit of a concentration of glucose is a pre-determined physiological value associated with the at least one physiological characteristic that can be stored on at least one database. In some embodiments, an at least one pre-determined physiological value associated with the at least one physiological characteristic retrieved from at least one database is a glucose measurement of 70 mg/dl (3.9 mmol/l). In some embodiments, an at least one pre-determined physiological value associated with the at least one physiological characteristic retrieved from at least one database is a glucose measurement of 80 mg/dl (4.4 mmol/l). In some embodiments, an at least one pre-determined physiological value associated with the at least one physiological characteristic retrieved from at least one database is a glucose measurement of between 80 mg/dl to 120 mg/dl (4.4 mmol/l to 6.7 mmol/l).

In some embodiments, an at least one pre-determined physiological value associated with the at least one physiological characteristic retrieved from at least one database is a glucose measurement of between 70 mg/dl to 110 mg/dl. In some embodiments, an at least one pre-determined physiological value associated with the at least one physiological characteristic retrieved from at least one database is a glucose measurement of between 70 mg/dl to 100 mg/dl. In some embodiments, an at least one pre-determined physiological value associated with the at least one physiological characteristic retrieved from at least one database is a glucose measurement of between 70 mg/dl to 90 mg/dl. In some embodiments, an at least one pre-determined physiological value associated with the at least one physiological characteristic retrieved from at least one database is a glucose measurement of between 70 mg/dl (3.9 mmol/L to 80 mg/dl (4.4 mmol/L). In some embodiments, an at least one pre-determined physiological value associated with the at least one physiological characteristic retrieved from at least one database is a glucose measurement of between 70 mg/dl (3.9 mmol/L) to 120 mg/dl (6.7 mmol/L). In some embodiments, an at least one pre-determined physiological value associated with the at least one physiological characteristic retrieved from at least one database is a glucose measurement of between 90 mg/dl to 120 mg/dl (6.7 mmol/L). In some embodiments, an at least one pre-determined physiological value associated with the at least one physiological characteristic retrieved from at least one database is a glucose measurement of between 100 mg/dl (5.6 mmol/L) to 120 mg/dl (6.7 mmol/L). In some embodiments, an at least one pre-determined physiological value associated with the at least one physiological characteristic is a glucose measurement of between 110 mg/dl (6.1 mmol/L) to 120 mg/dl. (6.7 mmol/L)

In some embodiments, the system of the present invention is configured to identify insulin excess, where insulin excess can result from the pharmacokinetic imperfections of any insulin preparation and/or insulin secretagogues used to treat diabetes in the context of an array of factors such as food intake, exercise, drug (including alcohol) interactions, altered sensitivity to insulin, and insulin clearance. As used herein, a "secretagogue" refers to a substance that causes another substance to be secreted, for example, but not limited to, sulfonylureas which are insulin secretagogues (i.e., triggering insulin release). In some embodiments, included physiological defenses against falling plasma glucose concentrations can result from the pathophysiology of glucose counterregulation, i.e., the mechanisms that normally prevent and/or rapidly correct hypoglycemia, at least in type-1 and/or advanced type-2 diabetes.

In some embodiments, the system of the present invention is configured to identify heart rate (HR) variability, which is typically used to detect autonomic dysfunction in clinical settings. In some embodiments, a dysfunction of the autonomic nervous system can be associated with increased mortality after myocardial infarction in patients with diabetes (i.e., type 1 and/or type 2 diabetes) and in the general population. In some embodiments, adults with type-1 diabetes may exhibit a marked decrease in the low-frequency component of heart rate variability during spontaneous nocturnal hypoglycemia. In some embodiments, a decrease in the low-frequency component of heart rate variability during spontaneous nocturnal hypoglycemia correlates with a decline in glucose concentration during hypoglycemic events by, e.g., but not limited to, exhibiting a significant, positive correlation with the decrease of the low-frequency component of HR variability (e.g., but not limited to, r=0.48; P=0.04). In some embodiments, the correlation of a decrease in the low-frequency component of heart rate variability with a decline in glucose concentration during hypoglycemic events can serve as a prediction mechanism, where additional medical and non medical parameters can be utilized as additional parameters in order to define a pathway for the HRV during the night, and hence to look for deviations from the pathway that will trigger a plurality of alerts, as such deviations may indicate a spontaneous nocturnal hypoglycemia.

In some embodiments, the present invention is an alert system configured to obtain/receive and/or store/record: (i) the last glucose reading prior to a user going to sleep, (ii) the food intake of the user, (iii) the medication taken by the user, and (iv) heart rate and/or heart rate variability parameters of the user. In an embodiment, the system is configured to calculate an expected heart rate and/or heart rate variability, and where an identification of extreme deviations from these values occurs, the system is configured to create and/or deliver a hypoglycemia alert to a user, an emergency contact(s), a doctor, a hospital, or any combination thereof. In some embodiments, the calculation of heart rate and/or heart rate variability occurs after a measurement of a person's heart rate is recorded by the system. In some embodiments, the system is configured to obtain, record, calculate, or any combination thereof, a plurality of measurements from a plurality of samples obtained during a plurality of time points. In some embodiments, the system is configured to operate without a blood glucose test. In some embodiments, the system is configured to allow an input of results derived from recent blood glucose test(s).

FIG. 3 illustrates an embodiment of the system of the present invention. FIG. 3 shows, as a non-limiting example, a wristband (the system of the present invention can also be combined in an armband or any other non-invasive wearable sensor) 710 worn by a user 720, where the wristband is configured to communicate by a communication standard such as, but not limited to, Bluetooth 730 with a mobile device such as, but not limited to, an iPhone 740. In an embodiment, the system includes a mobile device 740 which is configured to incorporate an application/software configured to capture a plurality of bio-signals, e.g., but not limited to, heart rate and the heart rate variability of a user, generated/obtained from the wristband 710. In an embodiment, the system is configured to obtain additional biosignals captured from a user's body from a plurality of sensors housed on the wristband including, but not limited to, blood oxygen, galvanic response, skin temperature, or any combination thereof.

FIG. 4 illustrates an embodiment of the system of the present invention, where the system is configured to calculate heart rate variability by use of, e.g., but not limited to, the mobile device, where the heart rate variability is measured and identified by the system when the frequency of the heart beat-to-beat sampling is sufficiently/substantially high, for example, but not limited to, a measurement of about 108 hz. In another embodiment, the system is configured to send information/data from an application/software to, e.g., but not limited to, a Data Center 750, where the Data Center manages Big Data analysis. In an embodiment, information/data is managed by: (i) being stored and/or compared to a plurality of users' data, (ii) benchmarking the user's data to the user's historical data, (iii) back-testing, (iv) storing, (v) routing data/information to medical personnel (e.g., but not limited to, doctors, nurses, nurse practitioners, EMTs, etc., or any combination thereof), or any combination thereof.

In some embodiments, the system of the present invention is configured to identify/measure a sudden drop in the heart rate variability and/or component(s) of heart rate variability (e.g., but not limited to, the low frequency component(s)), where the sudden drop in the heart rate variability and/or component of heart rate variability is/are an indication(s) of a forthcoming hypoglycemic event. In some embodiments, the system includes an alert configured to trigger an alarm on, e.g., but not limited to, at least one mobile phone. In another embodiment, the system is configured to alert the user to wake-up and eat and/or drink a carbohydrate containing food stuff (i.e., any food stuff that, when metabolized by the user, will provide sugar to the user). In some embodiments, the system is configured to send at least one alert/a plurality of alerts to at least one medical team and/or at least one family member of the user. In some embodiments, the system is configured to remind/alert a user to test the user's glucose level before the user drinks and/or eats. In some embodiments, the system is configured to remind/alert a user to test the user's glucose level after the user drinks and/or eats. In some embodiments, the application/software of the system is configured to receive an input/entry or a plurality of inputs/entries of the user's glucose level(s) into the application, where the input(s)/entry(ies) allow for the application/software to adjust and learn to adjust itself, if required.

FIG. 5 illustrates an embodiment of the system of the present invention, including an initial setting up phase 9.1, where the system is configured to receive a plurality of inputs provided/delivered by a user which define his preference set, for example, but not limited to, medications, including dosing and morning/afternoon/evening medication, favorite foods, glycemic index for different foods if needed, for example, when the user's known digestion is different from the otherwise known glycemic index. In another embodiment, at step 9.2, the system is configured to receive a user's entry/input, where the user's entry/input can be the user's last food intake before going to sleep, as well as the information related to last glucose reading before going to sleep, stress level (if, for example, the wrist band was not worn during the day and the information was not captured during the day by the system already), information regarding insulin and other medications taken and which might still be influencing the glucose level in his body (such as, e.g., but not limited to, stress and anxiety reducing medication). In an embodiment, at stage 9.3, the system is configured to continuously analyze information/data input and/or collected from the wrist band. In another embodiment, the information/data can include multi-parameters from at least one of the following measurements: beat-to-beat heart rate, heart rate variability and heart rate variability components, oxygen level, skin temperature, galvanic skin response, or any combination thereof. In another embodiment, the system is configured to analyze the information/data for changes/deviations compared with an expected information/data projected for the same time during the night sleep for the same user when compared to a benchmark on the data base, which is located at the mobile device 740 and the data center 750 and/or the cpu level located on the wrist band 710. In some embodiments, the expected value can be derived many different ways, for example using the historical pattern of the same user or similar users or patients given similar scenarios of food intake and glucose readings before going to sleep. In an embodiment, by way of non-limiting illustration, the pattern of a person of a Type II diabetic with a glucose reading prior to going to sleep of 100 and an average stress day can be compared to the average population pathway. In some embodiments, a pathway of a reading of 120 with a stressful day (as measured by, e.g., but not limited to, questionnaires and HRV or galvanic skin readings) and an evening meal filled with carbs will be compared to a population of similar pattern. In some embodiments, pattern recognition and parameters of interest may correlate to the above parameters but can correlate to combination of parameters, as such parameters may arise from statistical analysis using tools such as discriminant or principal component analysis. In an embodiment, the system is configured to compare the calculated expected values with the actual. In an embodiment, the system is configured to receive/record/account the prior information known about the user, such as, but not limited to, the food eaten in the meal prior to going to sleep, the glucose level as tested prior to going to sleep, in the tests measured on the day(s) preceding, or any combination thereof. In an embodiment, the system is configured to trigger and/or send at least one alert (e.g., 1, 2, 3, 4, 5, 6, 7, 8, 9, 10 etc. alerts) when, according to the comparison of the system noted in 9.5, there is a substantially significant change from what would have been expected, to: wake up the person 9.6.1, to alert the family, 9.6.2, alert the medical team 9.6.3, or any combination thereof.

In another embodiment, the system of the present invention includes triggers for an alarm which is configured to be adjusted based on the habits of the user. In an embodiment, the system is configured to receive (i) food entries from the user, where the food entries were consumed before going to sleep, where the software/application is configured to calculate the amount and/or type of carbohydrates, (ii) medication entries from the user (including, but not limited to, Bolus and Basal insulin brand and dosing), (iii) any personal settings, or any combination thereof.

In some embodiments, the amount of food and medication prior to going to sleep will have an impact on the probability of hypoglycemia and the time during sleep, if at all, of an hypoglycemia event to occur. In some embodiments, additional events on the day prior to the night sleep influence the likelihood of hypoglycemia to occur. In some embodiment, levels of stress are configured to be measured by the wristband by the HRV that was measured during the preceding day, as captured by the application/software of the system. In an embodiment, there is a correlation between higher the level of stress and the higher occurrence for a hypoglycemic event. In some embodiments, loss/reduction of autonomic function can result in a reduction in HRV may also have negative effects on the user's body's ability to process and/or store glucose.

The Autonomic Nervous System

Table 1 outlines which organs are affected by the sympathetic (SNS) and parasympathetic (PSNS) nervous systems. Typically, the SNS initiates a "fight or flight" response to stress. The SNS increases heart rate, dilates or opens the lungs, inhibits digestion and dilates the pupils, providing the body with the resources it needs to protect itself in times of danger. The PSNS conversely, is known as the "rest and digest" system; it promotes digestion, reduces heart rate, increases salivation, increases urine secretion from the kidneys and constricts the pupils. On a day-to-day basis, these two pathways work in parallel to maintain homeostatic balance within the body.

TABLE 1

| Hormone | Blood glucose | Mechanism of Action | |
| --- | --- | --- | --- |
| | | Inhibition of gluconeogenesis (liver) | Glucose entry stimulation (muscle) |
| Insulin | ↓ | Stimulation of glucose storage, glycogen formation (liver, muscle) | — |
| Adrenaline | ↑ | — | Stimulation of glycogen breakdown to active molecules (liver, muscle) |
| Glucagon | ↑ | Stimulation of glucose storage (liver) Stimulation of glucose formation from non-carbohydrate substrates (liver) | — |
| Cortisol | ↑ | — | Stimulation of glucose formation from non-carbohydrate substrates (liver) |
| Growth hormone | ↑ | — | Mobilization of triglycerides |

Glucose

Glucose levels in the blood and tissues are maintained via a series of different processes, largely stimulated by different hormones. Ingested food is broken down by enzymes into simple sugars (monosaccharides), which are absorbed through the gut wall and transported to the liver. Glucose can directly enter the liver, brain, kidney and red blood cells. It uses insulin to enter muscle and adipose (fat) tissue cells. In the liver and muscle cells glucose is converted to glycogen, its storage form. The reverse process is the degradation of glycogen to form glucose and glucose-6-phosphate (G6P). In muscle, G6P is used to produce ATP, the unit of energy required for contraction. Glucose may also be used for the synthesis of other substances such as glycoproteins and glycolipids or it may be transformed into fat and stored as adipose tissue. All of these processes work together to maintain a normal range of blood glucose, from 3.8 to 6.1 mmol/L. Table 1 summarizes the effects of different hormones on blood glucose levels.

The Autonomic Nervous System & Glucose

In healthy individuals, when blood glucose levels fall the SNS is activated, stimulating glucose production in the liver and kidney and reducing muscle use of glucose by way of adrenaline release. Vagal (parasympathetic) stimulation has the opposite effect: insulin release from the pancreas, which stimulates glucose uptake by cells; reduction in glucose release from tissues and increased glycogen formation by the liver. Hypoglycemia, or low blood sugar, leads to sympathetic activation increasing blood glucose levels, while hyperglycaemia, high blood sugar, results in parasympathetic activation to reduce blood glucose levels. These two systems work in unison to maintain healthy blood glucose levels. Therefore, impaired parasympathetic regulation (decreased HRV) increases risk for chronic hyperglycaemia and hyperinsulinemia (raised insulin levels, also known as insulin resistance), which is a pre-cursor for diabetes mellitus.

Diabetes & Heart Rate Variability (HRV)

In some embodiments, the system of the present invention is configured to identify a correlation between insulin resistance and HRV; specifically, diabetic patients (DM) show lower than average HRV. In some embodiments, the system can include parameters such as, but not limited to, the disease background of the diabetes patient when calculating the expected values of the HRV throughout the night. In some embodiments, a correlation exists between insulin resistance (as indicated by raised fasting serum insulin levels) and reduced HRV; specifically, an overall decline in HRV in both diabetic and non-diabetic populations can occur, with a greater decrease in participants with diabetes. In some embodiments, there is an increased risk among diabetics for autonomic neuropathies can lead to loss of sensation in the peripheries and in extreme cases, infected wounds resulting in limb loss (often known as diabetic foot). In some embodiments, there are correlations between HRV and insulin sensitivity, diabetes, fasting blood glucose and even glycosylated hemoglobin (HbA1c). In some embodiments, diabetic subjects have a more rapid temporal decrease in HRV conditional on baseline HRV than nondiabetic subjects, e.g., but not limited to: adjusted mean annual changes (95% CI) (ms/year) in the SD (i.e., standard deviation) of all normal-to-normal R-R (i.e., interbeat) intervals can be −0.65 (−0.69 to −0.61) for those with normal fasting glucose vs. −0.95 (−1.09 to −0.81) for diabetic subjects, in root mean square of successive differences in normal-to-normal R-R intervals −0.35 (−0.39 to −0.30) vs. −0.66 (−0.82 to −0.51), and in R-R interval 6.70 (6.37-7.04) vs. 3.89 (2.72-5.05). In some embodiments, HRV of severely obese patients with insulin resistance can improve once the patient has a gastric bypass and/or has a decrease in insulin resistance. In some embodiments, the normal-to-normal R-R intervals can be −0.69 to −0.65 in individuals with normal fasting glucose. In some embodiments, the normal-to-normal R-R intervals can be −0.65 to −0.61 in individuals with normal fasting glucose. In some embodiments, the R-R intervals can be −1.00 to −0.81 for diabetic subjects. In some embodiments, the R-R intervals can be −0.90 to −0.81 for diabetic subjects. In some embodiments, the R-R intervals can be −1.09 to −0.9 for diabetic subjects. In some embodiments, the R-R intervals can be −1.09 to −1 for diabetic subjects. In some embodiments, the root mean square of successive differences in normal-to-normal R-R intervals can be −0.39 to −0.35 in individuals with normal fasting glucose. In some embodiments, the root mean square of successive differences in normal-to-normal R-R intervals can be −0.35 to −0.30 in individuals with normal fasting glucose. In some embodiments, the root mean square of successive differences in diabetic subjects can be −0.7 to −0.51. In some embodiments, the root mean square of successive differences in diabetic subjects can be −0.6 to −0.51. In some embodiments, the root mean square of successive differences in diabetic subjects can be −0.82 to −0.6. In some embodiments, the root mean square of successive differences in diabetic subjects can be −0.82 to −0.7. In some embodiments, the R-R interval in individuals with normal fasting glucose can be 6.5-7.04. In some embodiments, the R-R interval in individuals with normal fasting glucose can be 6.8-7.04. In some embodiments, the R-R interval in individuals with normal fasting glucose can be 6.37-6.8. In some embodiments, the R-R interval in individuals with normal fasting glucose can be 6.37-6.5. In some embodiments, the R-R interval in diabetic subjects can be 3-5.05. In some embodiments, the R-R interval in diabetic patients can be 4-5.05. In some embodiments, the R-R interval in diabetic subjects can be 2.72-4. In some embodiments, the R-R interval in diabetic subjects can be 2.72-3.

Illustrative Operating Environments

FIG. 1 illustrates one embodiment of an environment in which the system of the present invention may operate. However, not all of these components may be required to practice the invention, and variations in the arrangement and type of the components may be made without departing from the spirit or scope of the present invention. In some embodiments, the system and method may include a large number of members and/or concurrent transactions. In other embodiments, the system and method are based on a scalable computer and network architecture that incorporates varies strategies for assessing the data, caching, searching, and database connection pooling. An example of the scalable architecture is an architecture that is capable of operating multiple servers.

In embodiments, members of the computer system 102-104 include virtually any computing device capable of receiving and sending a message over a network, such as network 105, to and from another computing device, such as servers 106 and 107, each other, and the like. In embodiments, the set of such devices includes devices that typically connect using a wired communications medium such as personal computers, multiprocessor systems, microprocessor-based or programmable consumer electronics, network PCs, and the like. In embodiments, the set of such devices also includes devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile device, and the like. Similarly, in embodiments, client devices 102-104 are any device that is capable of connecting using a wired or wireless communication medium such as a PDA, POCKET PC, wearable computer, and any other device that is equipped to communicate over a wired and/or wireless communication medium.

In embodiments, each member device within member devices 102-104 may include a browser application that is configured to receive and to send web pages, and the like. In embodiments, the browser application may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In some embodiments, programming may include either Java, .Net, QT, C, C++ or other suitable programming language.

In embodiments, member devices 102-104 may be further configured to receive a message from another computing device employing another mechanism, including, but not limited to email, Short Message Service (SMS), Multimedia Message Service (MMS), instant messaging (IM), internet relay chat (IRC), mIRC, Jabber, and the like or a Proprietary protocol.

In embodiments, network 105 may be configured to couple one computing device to another computing device to enable them to communicate. In some embodiments, network 105 may be enabled to employ any form of computer readable media for communicating information from one electronic device to another. Also, in embodiments, network 105 may include a wireless interface, and/or a wired interface, such as the Internet, in addition to local area networks (LANs), wide area networks (WANs), direct connections, such as through a universal serial bus (USB) port, other forms of computer-readable media, or any combination thereof. In embodiments, on an interconnected set of LANs, including those based on differing architectures and protocols, a router may act as a link between LANs, enabling messages to be sent from one to another.

Also, in some embodiments, communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art. Furthermore, in some embodiments, remote computers and other related electronic devices could be remotely connected to either LANs or WANs via a modem and temporary telephone link. In essence, in some embodiments, network 105 includes any communication method by which information may travel between client devices 102-104, and servers 106 and 107.

FIG. 2 shows another exemplary embodiment of the computer and network architecture that supports the method and system. The member devices 202a, 202b thru 202n shown each at least includes a computer-readable medium, such as a random access memory (RAM) 208 coupled to a processor 210 or FLASH memory. The processor 210 may execute computer-executable program instructions stored in memory 208. Such processors comprise a microprocessor, an ASIC, and state machines. Such processors comprise, or may be in communication with, media, for example computer-readable media, which stores instructions that, when executed by the processor, cause the processor to perform the steps described herein. Embodiments of computer-readable media may include, but are not limited to, an electronic, optical, magnetic, or other storage or transmission device capable of providing a processor, such as the processor 210 of client 202a, with computer-readable instructions. Other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript.

Member devices 202a-n may also comprise a number of external or internal devices such as a mouse, a CD-ROM, DVD, a keyboard, a display, or other input or output devices. Examples of client devices 202a-n may be personal computers, digital assistants, personal digital assistants, cellular phones, mobile phones, smart phones, pagers, digital tablets, laptop computers, Internet appliances, and other processor-based devices. In general, a client device 202a may be any type of processor-based platform that is connected to a network 206 and that interacts with one or more application programs. Client devices 202a-n may operate on any operating system capable of supporting a browser or browser-enabled application, such as Microsoft™, Windows™, or Linux. The client devices 202a-n shown may include, for example, personal computers executing a browser application program such as Microsoft Corporation's Internet Explorer™, Apple Computer, Inc.'s Safari™, Mozilla Firefox, and Opera. Through the client devices 202a-n, users, 212a-n communicate over the network 206 with each other and with other systems and devices coupled to the network 206. As shown in FIG. 1B, server devices 204 and 213 may be also coupled to the network 206.

In some embodiments, the term "mobile electronic device" may refer to any portable electronic device that may or may not be enabled with location tracking functionality. For example, a mobile electronic device can include, but is not limited to, a mobile phone, Personal Digital Assistant (PDA), Blackberry™, Pager, Smartphone, or any other reasonable mobile electronic device. For ease, at times the above variations are not listed or are only partially listed, this is in no way meant to be a limitation.

In some embodiments, the terms "proximity detection," "locating," "location data," "location information," and "location tracking" as used herein may refer to any form of location tracking technology or locating method that can be used to provide a location of a mobile electronic device, such as, but not limited to, at least one of location information manually input by a user, such as, but not limited to entering the city, town, municipality, zip code, area code, cross streets, or by any other reasonable entry to determine a geographical area; Global Positions Systems (GPS); GPS accessed using Bluetooth™; GPS accessed using any reasonable form of wireless and/or non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink-Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed, this is in no way meant to be a limitation.

In some embodiments, near-field wireless communication (NFC) can represent a short-range wireless communications technology in which NFC-enabled devices are "swiped," "bumped," "tap" or otherwise moved in close proximity to communicate. In some embodiments, NFC could include a set of short-range wireless technologies, typically requiring a distance of 10 cm or less.

In some embodiments, NFC may operate at 13.56 MHz on ISO/IEC 18000-3 air interface and at rates ranging from 106 kbit/s to 424 kbit/s. In some embodiments, NFC can involve an initiator and a target; the initiator actively generates an RF field that can power a passive target. In some embodiment, this can enable NFC targets to take very simple form factors such as tags, stickers, key fobs, or cards that do not require batteries. In some embodiments, NFC peer-to-peer communication can be conducted when a plurality of NFC-enable devices within close proximity of each other.

In some embodiments, in addition to the glucose level, additional parameters can be used for the prediction of the hypoglycemia.

In some embodiments, the instant invention provides for a computer system, including: a) at least one server having software stored on a non-transient computer readable medium; where, upon execution of the software, the at least one server is at least configured to: i) receiving, an input from a user, where the input includes user data consisting of: food intake of the user, glucose readings of the user, medication intake by the user, stress related events in the preceding day, insulin dose taken by the user, or any combination thereof; ii) receiving, in real-time, physiological data representative of at least one physiological measurement of at least one physiological characteristic of the user, where the at least one physiological characteristic is selected from the group consisting of: heart rate, heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a computer method, including: i) receiving, an input from a user or from his medical record, where the input comprises user data consisting of: food intake of the user, stress related events in the preceding day, glucose readings of the user, medication intake by the user, insulin dose taken by the user, or any combination thereof; ii) receiving, in real-time, physiological data representative of at least one physiological measurement of at least one physiological characteristic of the user, where the at least one physiological characteristic is selected from the group consisting of: heart rate, heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a computer system, including: a) at least one server having software stored on a non-transient computer readable medium; where, upon execution of the software, the at least one server is at least configured to: i) receiving, in real-time, an input from a user, where the input includes user data consisting of: food intake of the user, glucose readings of the user, medication intake by the user, insulin dose taken by the user, or any combination thereof; ii) receiving, in real-time, physiological data representative of at least one physiological measurement of at least one physiological characteristic of the user, where the at least one physiological characteristic is selected from the group consisting of: heart rate, heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

In some embodiments, the instant invention provides for a computer method, including: i) receiving, in real-time, an input from a user, where the input comprises user data consisting of: food intake of the user, glucose readings of the user, medication intake by the user, insulin dose taken by the user, or any combination thereof; ii) receiving, in real-time, physiological data representative of at least one physiological measurement of at least one physiological characteristic of the user, where the at least one physiological characteristic is selected from the group consisting of: heart rate, heart rate variability, oxygen saturation, temperature, galvanic skin response, or any combination thereof; iii) comparing, in real-time, the at least one physiological measurement of the user to at least one pre-determined physiological value associated with the at least one physiological characteristic retrieved from at least one database; iv) based on the comparing, determining, in real-time, that a difference between the at least one physiological measurement of the user and the at least one pre-determined physiological value is: a) higher than a predetermined threshold value, or b) smaller than the predetermined threshold value, and then: v) generating, in real-time, at least one alert when the at least one pre-determined physiological value is higher than the predetermined threshold value; vi) transmitting, in real-time, the at least one alert to at least one of: the user, at least one family member, at least one medical practitioner, or any combination thereof; and vii) when the at least one pre-determined physiological value is smaller than the predetermined threshold value, causing to continue measuring, in real-time, the at least one physiological characteristic of the user.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is claimed is:

1. A system, comprising:
at least one user-wearable device, wherein the at least one user-wearable device is in contact with a skin of a user when the user wears the at least one user-wearable device, and wherein the at least one user-wearable device comprises at least one sensor configured to acquire physiological measurements for at least one hypoglycemia-related physiological characteristic of the user that is correlated with at least one of a blood insulin excess or a hypoglycemic blood glucose level;

wherein the at least one hypoglycemia-related physiological characteristic is chosen from beat-to-beat heart rate, heart rate variability, oxygen saturation, galvanic skin response, and any combination thereof;

a non-transient computer readable medium having hypoglycemia-predictive software;

at least one processor configured to execute the hypoglycemia-predictive software;

wherein, upon execution of the hypoglycemia-predictive software, the at least one processor is at least configured to:

receive, in real-time, user-specific data from a user, wherein the user-specific data comprises: food intake of the user, glucose readings of the user, medication intake by the user, user behavior data and at least one insulin dose taken by the user;

receive, in real-time, from the at least one user-wearable device, user-specific hypoglycemia-related physiological data, comprising at least one particular physiological measurement of the at least one hypoglycemia-related physiological characteristic of the user;

determine, in real-time, a hypoglycemic event of the user, based on the at least one particular physiological measurement of the at least one hypoglycemia-related physiological characteristic of the user and at least one chosen from:
1) a predicted user-specific value of the at least one hypoglycemia-related physiological characteristic, determined based on the user-specific data, and
2) an expected population-based value of the at least one hypoglycemia-related physiological characteristic, determined based on a population of individuals identified based on the user-specific data;

generate, in real-time, in response to the determination of the hypoglycemic event of the user, at least one alert, instructing the user to consume glucose-rich intake; and output, in real-time, the at least one alert to at least one of: the user, at least one family member, at least one medical practitioner, or any combination thereof.

2. A method, comprising:

providing at least one user-wearable device, wherein the at least one user-wearable device is in contact with a skin of a user when the user wears the at least one user-wearable device, and wherein the at least one user-wearable device comprises at least one sensor configured to acquire physiological measurements for at least one hypoglycemia-related physiological characteristic of the user that is correlated with at least one of a blood insulin excess or a hypoglycemic blood glucose level;

wherein the at least one hypoglycemia-related physiological characteristic is chosen from beat-to-beat heart rate, heart rate variability, oxygen saturation, galvanic skin response, and any combination thereof;

receiving, by a processor executing hypoglycemia-predictive software, in real-time, user-specific data from a user, wherein the user-specific data comprises: food intake of the user, glucose readings of the user, medication intake by the user, user behavior data and at least one insulin dose taken by the user;

receiving, by the processor executing hypoglycemia-predictive software, in real-time, from the at least one user-wearable device, user-specific hypoglycemia-related physiological data, comprising at least one particular physiological measurement of the at least one hypoglycemia-related physiological characteristic of the user;

determining, by the processor executing hypoglycemia-predictive software, in real-time, a hypoglycemic event of the user, based on the at least one particular physiological measurement of the at least one hypoglycemia-related physiological characteristic of the user and at least one chosen from:
1) a predicted user-specific value of the at least one hypoglycemia-related physiological characteristic, determined based on the user-specific data, and
2) an expected population-based value of the at least one hypoglycemia-related physiological characteristic, determined based on a population of individuals identified based on the user-specific data;

generating, by the processor executing hypoglycemia-predictive software, in real-time, in response to the determination of the hypoglycemic event of the user, at least one alert, instructing the user to consume glucose-rich intake; and outputting, by the processor executing hypoglycemia-predictive software, in real-time, the at least one alert to at least one of: the user, at least one family member, at least one medical practitioner, or any combination thereof.

3. The system of claim 1, wherein the user is in a state of sleep.

4. The system of claim 3, wherein the at least one alert comprises at least one sleep-awaking software instruction to a computing device associated with the user to cause the computing device to generate an output that is configured to awake the user from the state of sleep.

5. The method of claim 2, wherein the user is in a state of sleep.

6. The method of claim 5, wherein the at least one alert comprises at least one sleep-awaking software instruction to a computing device associated with the user to cause the computing device to generate an output that is configured to awake the user from the state of sleep.

* * * * *